United States Patent [19]

Cane et al.

[11] 4,342,627
[45] Aug. 3, 1982

[54] DEHYDRATION OF ALCOHOLS

[75] Inventors: Charles Cane; Bertram Yeomans, both of Hull, England

[73] Assignee: BP Chemicals Limited, London, England

[21] Appl. No.: 254,740

[22] Filed: Apr. 16, 1981

[30] Foreign Application Priority Data

Apr. 17, 1980 [GB] United Kingdom ............... 8012619

[51] Int. Cl.³ .................. B01D 3/36; C07C 29/82; C07C 31/08
[52] U.S. Cl. .................................. 203/19; 203/39; 203/53; 203/60; 203/68; 203/69; 203/70; 203/82; 203/83; 203/97; 203/DIG. 13; 568/916
[58] Field of Search .................. 203/19, 18, 39, 76, 203/75, 83, 82, 92–97, 53, 60, 69, 68, 70, 52, DIG. 13; 568/916

[56] References Cited

U.S. PATENT DOCUMENTS

| | | | |
|---|---|---|---|
| 1,586,717 | 6/1926 | Steffens | 203/19 |
| 1,763,722 | 6/1930 | Ricard | 203/19 |
| 1,831,425 | 11/1931 | Ricard | 203/19 |
| 2,017,067 | 10/1935 | Kraft | 203/19 |
| 2,666,736 | 1/1954 | Robertson et al. | 203/83 |
| 3,303,108 | 2/1967 | Rauch et al. | 203/18 |
| 3,960,672 | 6/1976 | Ester et al. | 203/83 |
| 4,161,429 | 7/1979 | Baiel | 203/18 |
| 4,256,541 | 3/1981 | Muller et al. | 203/19 |

FOREIGN PATENT DOCUMENTS 644956  5/1937  Fed. Rep. of Germany ........ 203/19

Primary Examiner—Wilbur L. Bascomb, Jr.
Attorney, Agent, or Firm—Brooks, Haidt, Haffner & Delahunty

[57] ABSTRACT

The present invention relates to a continuous process for producing substantially anhydrous alcohols from aqueous solutions thereof by distilling a mixture of aqueous alcohol and an entrainer to a drying column withdrawing an azeotrope as a distillate and continuously recovering anhydrous alcohol with less than 0.1% by weight of water from the base of the drying column. The improvement resides in feeding the distillate to a condenser and introducing (a) the condensate therefrom in a substantially non-turbulent state into a decanter at a point close to the interface between the aqueous and organic phases present therein and (b) a specified amount of water, which is less than 0.25 volumes per volume of the anhydrous alcohol recovered, into the drying column at a point adjacent to that at which the organic hydrocarbon phase is returned as reflux. The main advantage of the process is that it gives considerable energy savings, is flexible with regard to the entrainer used and can be incorporated in existing plants.

9 Claims, 1 Drawing Figure

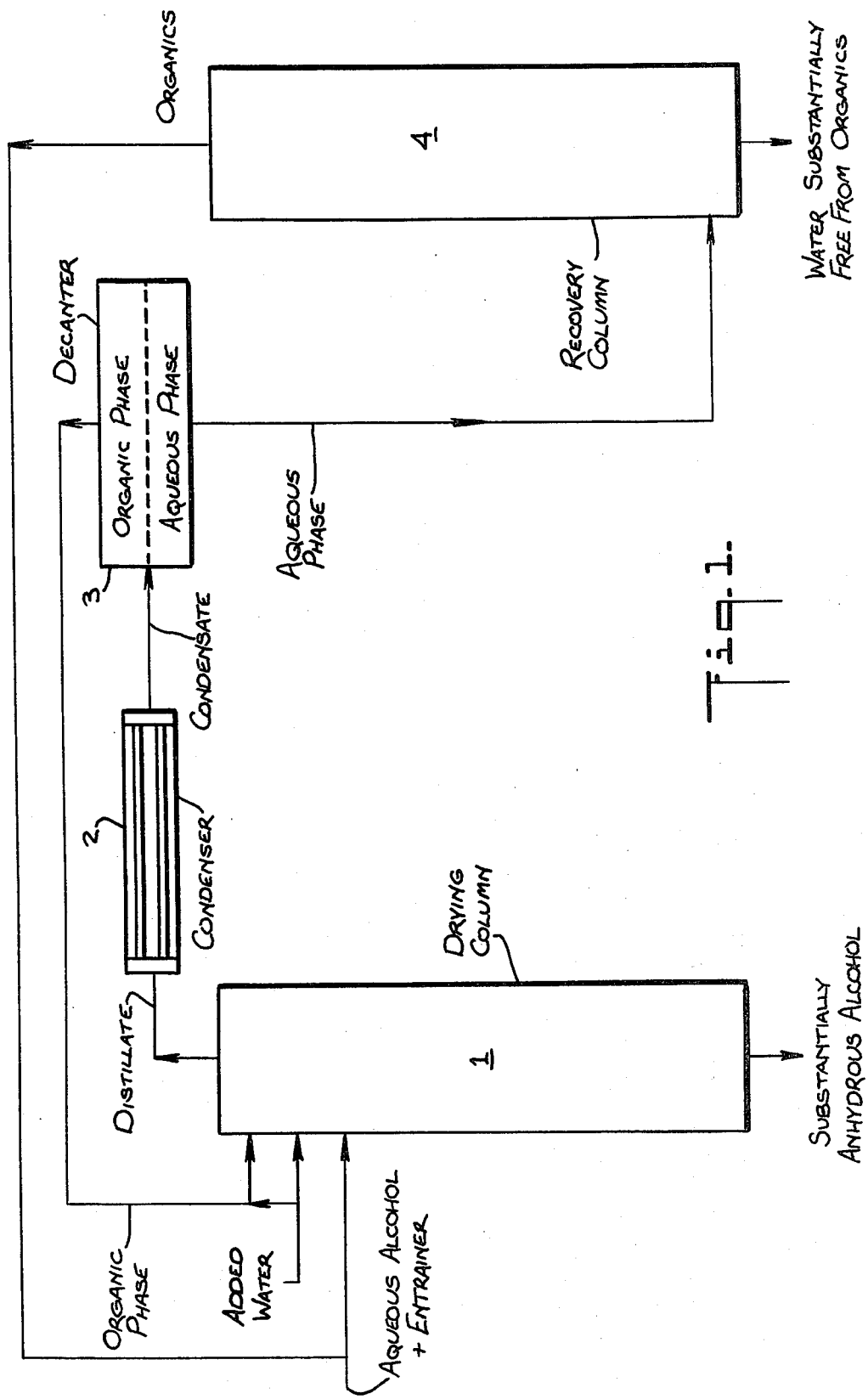

DEHYDRATION OF ALCOHOLS

The present invention relates to improvements in processes for the removal of water from aqueous alcohols, particularly from alcohols which form azeotropic mixtures with water and an entrainer.

Various methods have been suggested for drying alcohols whether obtained from fermentation or synthetic processes. One such method is azeotropic distillation using an entrainer. Several entrainers have been used for this purpose including glycols and hydrocarbon solvents. Of the hydrocarbon solvents, benzene has hitherto been the most widely used. The rate of phase separation of azeotropic distillates containing benzene is very slow. This drawback has been overcome by using n-heptane in conjunction with benzene to form a quaternary azeotrope. However, such quaternary azeotropes containing n-heptane take overhead a smaller amount of water relative to benzene thus reducing the efficiency of the drying process. An additional problem has also been noted with the separation of the aqueous and organic phases from the distillate fed into a decanter. In some instances, in spite of using high boil-up ratios (boil-up ratio is the amount of azeotrope product taken overhead to the amount of dried final product removed from the base of the drying column) the apparent rapid initial separation of the phases is deceptive in that the organic layer still contains a significant amount of water. This inefficiency becomes apparent if the organic phase recovered from the initial separation is allowed to stand in a cool environment for a few days when a further aqueous layer separates. The amount of water in this further aqueous layer using conventional entrainers such as benzene and cyclohexane is between 3.5 and 5.0% by weight of the organic layer recovered. Therefore an undesirably large volume of this organic layer has to be returned to the drying column as reflux and hence the separation efficiency of the column is reduced in spite of using very long columns and high boil-up ratios. Moreover, high energy inputs are necessary to achieve the desired separation. In the case of benzene entrainer, substantially complete separation has not been achieved in spite of allowing several hours for phase separation. In a continuous process for producing ethanol commercially, it is not feasible to allow such inordinately long periods for separation of the phases because in such circumstances the decanter capacity will have to be huge in relation to the rest of the plant. This creates problems of space and capital costs.

Replacement of benzene by entrainers such as cyclohexane gives a relatively quicker separation of layers but is associated with other problems. For example, the energy inputs on using cyclohexane are greater than those required for benzene. Moreover, cyclohexane-ethanol-water mixtures suffer from the phenomenon of colloid formation. Once such colloids are formed, it is virtually impossible to coagulate the colloid and achieve complete phase separation in the decanter. The process described in our published European Patent Application No. 0001681 mitigates to a considerable extent the problems associated with benzene and cyclohexane and achieves a commercially viable drying process for ethanol without incurring excessive capital and energy costs.

It has now been found, to our surprise, that by the addition of controlled amounts of water to the drying column in addition to the feed and conventional reflux, the energy inputs into the distillation and drying process may be further reduced without adversely affecting the quality of the product and at the same time increasing the flexibility of the process in respect of the entrainer used.

Accordingly, the present invention is a continuous process for producing substantially anhydrous alcohols from aqueous solutions thereof comprising distilling a mixture of aqueous alcohol and an entrainer fed to the upper half of a drying column, withdrawing an azeotrope as an overhead distillate and continuously recovering substantially anhydrous alcohol containing not more than 0.1% by weight of water from the base of the drying column, feeding the distillate into a condenser to produce a condensate, introducing the condensate in a substantially non-turbulent state into a decanter at a point close to the interface between the aqueous and organic phases present therein to allow separation of the phases, recycling the organic hydrocarbon phase to the top of the drying column and simultaneously introducing into the drying column at a point adjacent to that at which the organic hydrocarbon phase is returned as reflux an amount of added water not greater than 0.25 volumes per volume of the anhydrous alcohol recovered, feeding the aqueous phase into the lower half of a recovery column, recycling an overhead distillate product containing predominantly organic compounds from the recovery column to be mixed with the feed to the drying column, and removing water substantially free from organics from the base of the recovery column.

FIG. 1 is a schematic diagram illustrating the process of the invention.

Aqueous alcohol and entrainer are fed to a drying column 1 containing more than 50 plates. The azeotropic distillate is removed from the drying column overhead and is introduced onto a condenser 2. The condensate is passed into a decanter 3 at the interface between the organic and aqueous phases. The aqueous phase from the decanter is fed into a recovery column 4. The organic phase from the decanter and the organics from the recovery column are returned and recycled to the drying column. The organic phase from the decanter is recycled to the top of the drying column either directly into the column or indirectly with added water. The organics from the recovery column is suitably recycled by mixing it with the feed to the drying column. Substantially anhydrous alcohol is removed from the base of the drying column and water substantially free from organics is removed from the base of the recovery column.

The alcohols which may be dried by the process of the present invention are suitably saturated aliphatic alcohols containing 2 or 3 carbon atoms. Ethanol is preferred. Therefore, the following detailed description is directed specifically towards drying crude aqueous ethanol, although it will be understood that the principle is applicable to lower aliphatic alcohols in general.

The feed to the drying column is a heterogeneous mixture of aqueous ethanol and an entrainer. The entrainer may be any of the conventional entrainers used for drying alcohols, suitably benzene or a mixture thereof with n-heptane, ethyl acetate or cyclohexane. Of these, cyclohexane is most preferred. Where cyclohexane is used as the entrainer the mixture suitably contains between 80% and 90% by weight of ethanol, between 3% and 10% by weight of water and between 5% and 10% of cyclohexane.

The drying column suitably contains more than 50 plates, preferably between 55 and 110 plates. The drying column most preferably contains 100 plates and in such a case the heterogeneous mixture of aqueous ethanol and the entrainer is suitably fed into the drying column at a point such that there are less than 50 plates, preferably at least 60 plates, above the feed point in the column.

Substantially anhydrous ethanol containing not more than 0.1% and preferably not more than 0.05% by weight of water is continually withdrawn from the base of the drying column.

The azeotropic distillate, which is suitably a ternary azeotrope, withdrawn overhead from the drying column suitably contains over 70% by weight of the entrainer, between 15 and 20% by weight of ethanol and between 2 and 7% by weight of water. This azeotropic distillate is then fed into a condenser. The distillate is thus converted into a condensate by maintaining the temperature in the condenser suitably below 60° C., preferably between 35° and 50° C. A preliminary phase separation already begins to occur in the condensate. To minimise any turbulence in the condensate during transfer thereof into the decanter, the transfer is suitably done through a wide-bore pipe, and at a point as close to the interface between aqueous and organic phases already present therein as possible. This also facilitates the coagulation of any colloidal dispersions that may have been formed during transference of the condensate. It is preferable to use the decanter in a horizontal orientation so that the condensate introduced therein has a relatively longer distance to travel prior to the respective phases being withdrawn from the decanter, thus giving the condensate maximum opportunity for phase separation. The phase separation may be further aided by controlling the rate of flow of the condensate into the decanter such that the residence time of the condensate in the decanter is at least 1 minute, preferably between 20 and 100 minutes. For ethanol, the decanter is suitably maintained below 60° C., preferably between 35° and 50° C. The use of cyclohexane as an entrainer facilitates rapid separation of the organic hydrocarbon phase from the aqueous phase in the decanter. For example, in the case of a ternary mixture containing ethanol, water and cyclohexane, the aqueous phase separation commences immediately on starting the settling period and is completed relatively rapidly.

On separation of these phases in the decanter, the organic hydrocarbon phase contains for instance between 10 and 15% by weight of ethanol and between 0.1 and 0.2% by weight of water. This phase is recycled to the top of the drying column.

One of the features of the present invention is the surprising effect achieved by the paradoxical introduction of added water into the drying column which is primarily responsible for removing water from an aqueous alcohol feed. The water is introduced into the drying column at a point adjacent to the point of return of the organic hydrocarbon phase as reflux to the column and the added water may be introduced either directly into the column or indirectly by adding it to the stream of the organic hydrocarbon phase being returned as reflux to the column. If introduced directly, the point of introduction of water is preferably at or above the point of return of the reflux to the column. The amount of added water is preferably between 0.05 and 0.15 volumes per volume of the anhydrous alcohol recovered from the column.

The aqueous phase from the decanter is fed to the lower part of the recovery column. The recovery column suitably contains between 30 and 40 plates. The aqueous phase from the decanter is preferably fed to a point between the 7th and 20th plate from the base of the column or the kettle. In this column, the organic content of the aqueous phase is distilled as overheads, preferably using a reflux ratio which is in the range of between 5:1 and 10:1. The overhead distillate from the recovery column suitably containing over 70% alcohol and between 15 and 30% of the entrainer is recycled to be mixed with the feed to the drying column. Water, substantially free from organics, is removed from the base of the recovery column which may be discharged as waste.

The principal advantages and reasons for energy savings achieved by the process of the present invention are as follows:

1. In view of the lower water content of the organic phase, which is the consequence of the improved mode of operation of the decanter, a smaller volume of this phase is returned as recycle to the drying column.

2. The smaller volume of organics returned as reflux is engaged more efficiently in azeotrope formation by the new feature of introducing added water into the column.

3. The water addition enables the azeotrope to be formed more easily because it appears to restore the optimum concentrations of the three components in the drying column necessary to from an azeotrope and therefore consumes much less energy to achieve the azeotrope.

4. The efficient operation of the decanter as now described ensures that a much lower concentration of the organics is present in the aqueous phase and consequently a lower input of energy is required to separate the organics from water in the recovery column.

5. The process is flexible with regard to the entrainer used without loss of efficiency either in terms of the energy inputs or in terms of product quality.

6. The new feature can be easily incorporated in existing plant designs without substantial modifications or capital investments.

The invention is further illustrated with reference to the following examples and comparative tests.

COMPARATIVE TEST NO. 1

Not According to the Invention

Ethanol:water azetrope (7.94 kg containing 0.48 kg of water) was fed over 20 hours onto the 40th plate (from the kettle) of a 100-plate Oldershaw Column (50 mm diameter) drying still which contained cyclohexane. Ethanol:cyclohexane:water azeotrope (30.73 kg of composition 27.9% w/w ethanol, 2.6% w/w water and 69.5% w/w cyclohexane) was taken overhead using a primary reflux ratio of 0.35:1, was condensed and the two phases which formed were separated in a 1.6 liter horizontal cylindrical decanter at 38° C. The decanter was designed to avoid turbulence during phase separation. Thus, the overhead condensate was introduced via a wide-bore pipe into one end of the decanter close to the interface and the separated phases were withdrawn from the opposite end of the decanter. Organic phase (20.55 kg of composition 7.7% w/w ethanol, 0.1% w/w water and 92.2% w/w cyclohexane) was recycled onto plate 90 of the drying still. Dry ethanol final product (7.39 kg containing 0.05% w/w water and <1 ppm of cyclohexane) was collected from the base of the drying still.

The aqueous phase from the drying still decanter (10.19 kg of composition 68.7% w/w ethanol, 7.7% w/w water and 23.6% w/w cyclohexane) was fed onto the 10th plate of a 35-plate Oldershaw column (50 mm diameter) recovery still. Ethanol:cyclohexane:water azeotrope mixture (8.64 kg containing 69.8% w/w ethanol, 3.5% w/w water and 26.7% w/w cyclohexane) was taken overhead using a reflux ratio of 4:1 and this was recycled onto plate 23 of the drying still column. Water (0.48 kg) was removed from the base of the recovery still.

The energy consumption of the drying and recovery stills was expanded mainly in taking overhead 5.61 kg and 5.85 kg respectively of azeotrope mixture per kilogram of dry ethanol final product.

EXAMPLE NO. 1

According to the Invention

The procedure described in Comparative Test No. 1 above was repeated except that an addition of water was made continuously to the top of the drying still.

Thus, ethanol:water azeotrope (8 kg containing 0.48 kg of water) was fed over 19 hours on to the 40th plate of a 100-plate Oldershaw column drying still containing cyclohexane. Water (0.57 kg) was also added onto the top plate of the column. Ethanol:cyclohexane:water azeotrope (22.78 kg of composition 20.2% w/w ethanol, 5.6% w/w water and 74.2% w/w cyclohexane) was taken overhead using a primary reflux ratio of 0.35:1, was then condensed and the two phases which subsequently formed were separated. Organic phase (16.97 kg of composition 3.4% w/w ethanol, 0.1% w/w water and 96.5% w/w cyclohexane) was recycled onto plate 90 of the drying still. Dry ethanol final product (7.52 kg containing 0.08% w/w and <1 ppm of cyclohexane) was collected from the base of the drying still.

The aqueous phase from the drying still decanter (5.82 kg of composition 69.3% w/w ethanol, 21.8% w/w water and 8.9% w/w cyclohexane) was fed onto the 10th plate of a 35-plate Oldershaw column recovery still. Ethanol:cyclohexane:water azeotrope mixture (4.77 kg containing 84.5% w/w ethanol, 4.6% w/w water and 10.9% w/w cyclo-hexane) was taken overhead using a reflux ratio of 4:1 and this was recycled onto plate 23 of the drying still. Water (1.05 kg) was removed from the base of the recovery still.

The energy consumption of the drying and recovery stills was expended mainly in taking overhead 4.09 kg and 3.17 kg respectively of azeotrope mixture per kilogram of dry ethanol final product which much less than that incurred in Comparative Test No. 1.

COMPARATIVE TEST NO. 2

Not According to the Invention

The procedure described in Comparative Test No. 1 above was repeated except that a mixture of benzene and n-heptane was used instead of cyclohexane as entrainer.

Thus, ethanol:water azeotrope (9.77 kg containing 0.586 kg of water) was fed over 24 hours onto the 40th plate of a 100-plate Oldershaw column (50 mm diameter) drying still containing benzene:n-heptane mixture. Ethanol:water:hydrocarbon azeotrope mixture (24.83 kg of composition 24.4% w/w ethanol, 4.7% w/w water, 61.9% w/w benzene and 9.0% w/w n-heptane) was taken overhead using a primary reflux ratio of 0.35:1, condensed and the two phases which formed were separated. Organic phase (21.37 kg of composition 19.5% w/w ethanol, 2.3% w/w water, 68% w/w benzene and 10.2% w/w n-heptane) was recycled onto plate 90 of the drying still. Dry ethanol final product (9.17 kg containing 0.08% w/w water and <1 ppm of hydrocarbon) was collected from the base of the drying still.

The aqueous phase from the drying still decanter (3.45 kg of composition 54.5% w/w ethanol, 19.4% w/w water, 24% w/w benzene and 2.1% w/w n-heptane) was fed onto the 10th plate of a 35-plate Oldershaw column recovery still. Ethanol:water:hydrocarbon azeotrope mixture (2.9 kg containing 65% w/w ethanol, 3.8% w/w water, 28.6% w/w benzene and 2.6% w/w n-heptane) was taken overhead using a reflux ratio of 4:1 and this was recycled onto plate 23 of the drying still. Water (0.58 kg) was removed from the base of the recovery still.

The energy consumption of the drying and recovery stills was expended mainly in taking overhead 3.66 kg and 1.58 kg respectively of azeotrope mixture as distillate per kilogram of dry ethanol final product.

EXAMPLE 2

According to the Invention

The procedure used in Comparative Test No. 2 above was repeated except that an addition of water was made continuously to the top of the drying still.

Thus, ethanol:water azeotrope (18.33 kg containing 1.1 kg of water) was fed over 47 hours onto the 40th plate of a 100-plate Oldershaw column drying still containing benzene:n-heptane mixture. Ethanol:water:hydrocarbon azeotrope (42.26 kg containing 18.9% w/w ethanol, 6.1% w/w water, 65.6% w/w benzene and 9.4% w/w n-heptane) was taken overhead using a reflux ratio of 0.35:1, was condensed and the two phases which formed were separated. Organic phase (35.2 kg of composition 12.8% w/w ethanol, 1.3% w/w water, 74.9% w/w benzene and 11% w/w n-heptane) was recycled onto plate 90 of the drying still. Dry ethanol final product (17.24 kg containing 0.08% w/w water and <1 ppm of hydrocarbon) was collected from the base of the drying still.

The aqueous phase from the drying still decanter (7.06 kg of composition 49.1% w/w ethanol, 30% w/w water, 19.6% w/w benzene and 1.3% w/w n-heptane) was fed onto the 10th plate of a 35-plate Oldershaw column recovery still. Ethanol:water:hydrocarbon azeotrope mixture (5.06 kg containing 68.5% w/w ethanol, 3.2% w/w water, 26.5% w/w benzene and 1.8% w/w n-heptane) was taken overhead using a reflux ratio of 4:1 and this was recycled onto plate 23 of the drying still. Water (1.99 kg) was removed from the base of the recovery still.

The energy consumption of the drying and recovery stills was expended mainly in taking overhead 3.31 kg and 1.47 kg respectively of azeotrope mixture as distillate per kilogram of dry ethanol final product, which was significantly less than that incurred in the Comparative Test No. 2 which was not according to the invention.

We claim:

1. A continuous process for producing substantially anhydrous alcohols from aqueous solutions thereof comprising distilling a mixture of aqueous alcohol and an entrainer fed to the upper half of a drying column, withdrawing an azeotrope as an overhead distillate and continuously recovering substantially anhydrous alcohol containing not more than 0.1% by weight of water from the base of the drying column, feeding the distillate into a condenser to produce a condensate, introducing the condensate into a decanter to obtain a separation of the phases, recycling the organic hydrocarbon phase to the top of the drying column, feeding the aqueous phase into the lower half of a recovery column, recycling an overhead distillate product containing predominantly organic compounds from the recovery column to be mixed with the feed to the drying column, and removing water substantially free from organics from the base of the recovery column, characterised in that the condensate is introduced in a substantially non-turbulent state into a decanter at a point close to the interface between the aqueous and organic phases present therein and an amount of added water not greater than 0.25 volumes per volume of the anhydrous alcohol recovered is simultaneously introduced into the drying column at a point the same as or adjacent to that at which the organic hydrocarbon phase is returned as reflux.

2. A process according to claim 1 wherein the alcohol is ethanol.

3. A process according to claim 1 wherein the feed to the drying column is a heterogeneous mixture of aqueous ethanol and an entrainer selected from benzene, a mixture of benzene and n-heptane, ethyl acetate and cyclohexane.

4. A process according to claim 3 wherein the heterogeneous mixture contains between 80% and 90% by weight of ethanol, between 3% and 10% by weight of water and between 5% and 10% of cyclohexane.

5. A process according to claim 1 wherein the drying column contains between 55 and 110 plates.

6. A process according to claim 5 wherein the drying column contains 100 plates and the heterogeneous mixture of aqueous ethanol and the entrainer is fed into the drying column at a point such that there are less than 50 plates above the feed point in the column.

7. A process according to claim 1 wherein the temperature of the condenser and the decanter is maintained below 60° C.

8. A process according to claim 1 wherein the amount of added water is between 0.05 and 0.15 volumes per volume of the anhydrous alcohol recovered from the column.

9. A process according to claim 1 wherein the aqueous phase from the decanter is fed to a point between the 7th and 20th plate from the base of the recovery column containing between 30 and 40 plates and the distillation carried out using a reflux ratio of between 5:1 and 10:1.

* * * * *